United States Patent [19]

Walls et al.

[11] 3,959,883

[45] June 1, 1976

[54] HAND CONTROL SYSTEM FOR POWER HAND TOOLS

[76] Inventors: Earl L. Walls, 6567 Avenida Manana, La Jolla, Calif. 92037; Verl O. Olson, P.O. Box 2035, La Mesa, Calif. 92041

[22] Filed: July 23, 1973

[21] Appl. No.: 381,636

[52] U.S. Cl. ............................ 32/27; 91/459; 173/46; 173/57; 173/163; 251/131
[51] Int. Cl.² ....................... A61C 1/05; A61C 1/08
[58] Field of Search ............... 415/503, 61; 91/459; 32/26, 27, 28; 173/12, 46, 163, 57; 251/131–136

[56] References Cited
UNITED STATES PATENTS

| | | | |
|---|---|---|---|
| 3,346,958 | 10/1967 | Sinatra et al. | 415/503 X |
| 3,449,831 | 6/1969 | Vandis | 32/26 |
| 3,543,405 | 12/1970 | Banhart | 32/26 |
| 3,567,330 | 3/1971 | Apelskog et al. | 415/503 X |

Primary Examiner—Ernest R. Purser
Attorney, Agent, or Firm—Neil F. Markva

[57] ABSTRACT

A hand control system for power hand tools comprises a manually operated control means for activating a low current electric signal and means for actuating an operation of the power tool. Circuit means are provided for sensing the low current electric signal when it is activated by the manually operated control means to provide a higher current operational signal to the tool actuating means. The manually operated control means may include various types of switch means. The finger-tip control means is located on a hand-piece unit of a power tool. The circuit means includes means for amplifying the low current electric signal and switching means for receiving an amplified current drive signal from the amplifying means and transmitting the higher current operational signal to the actuating means. A specific feature of this invention is the use of the manually operated control means in combination with a dental device having an air driven motor for tool members rotatably mounted in the hand-piece unit.

82 Claims, 26 Drawing Figures

HAND CONTROL SYSTEM FOR POWER HAND TOOLS

BACKGROUND OF THE INVENTION

This invention relates to a hand control system for power hand tools. More specifically, the invention is directed to a hand control system for dental drive and medical or surgical drive systems.

There are numerous types of control systems for power tools such as dental drive and medical and surgical power tools. In such a prior art system, there are several basic functions which may be performed. These include providing a supply of air, water or other gaseous and liquid mediums and controlling the operation of a tool member.

More particularly, the control system of this invention is used in power tools having a hand-piece unit. The power tool may include a rotatable tool member mounted in the hand-piece unit and an air driven motor for rotating the tool member. In a dental device, the hand-piece unit includes a drill bit chuck, belt and pulleys to rotate the drill bit chuck or an air driven vane type motor assembled to a tubular, pencil-type handle. The tool members may comprise drill bits, rotary saws, rotary files, grinding wheels and the like. Tool members are mounted on the hand-piece unit to perform various functions related to the dental or medical professions.

Various types of control systems are used in the prior art to operate the various functions of the power tool. The most common type of control system comprises a foot-actuated control valve which regulates the amount of air and/or water to be supplied to the hand-piece unit. This water or air supply operation is accomplished either by pressing an air control foot pedal and/or a water control foot pedal of the foot-actuated control mechanism. Prior art dental or medical drive cabinets include various types of components such as air and water filters, metering valves, gauges, and related apparatus that provides the interconnection between the incoming supply air and water, the foot-actuated control valve assembly, the hand-piece unit and water syringe.

It is also known in the prior art to use hand control systems for power hand tools having a hand-piece unit. These known hand control systems, however, simply include an on-off switch. There is no particular type of circuit means for sensing a low current electric signal which is activated by a control means to provide a higher current operational signal to actuate the operation of the power tools.

In one such prior art hand control mechanism disclosed in U.S. Pat. No. 3,346,958, the operator of the hand-piece unit touches a recessed button located thereon. The operator's hand itself acts as a path for the current which completes the circuit back to the electrical system thereby actuating the various operations of the power tool. This particular system has many disadvantages such as not being able to offer a finger-tip controlled, modulated system for varying the speed of the tool members. Furthermore, there is no possibility of the use of a separate switching control assembly which may be attached to existing hand-piece units. It is further noted that where speed control is desired, the foot control system is used instead of relying upon a manually operated mechanism.

PURPOSE OF THE INVENTION

The primary object of this invention is to provide a hand control system for power hand tools which eliminates the necessity for using conventional foot-actuated control systems.

Another object of the invention is to provide a finger-tip modulated control system which may be used to control numerous operations of the power tool.

A further object of this invention is to provide a finger-tip control system incorporating various types of switches used in conjunction with circuit means for supplying very low current electric command signals which are maintained within an acceptable health-safety range of the dental and medical profession which is known to be less than about 10 micro amps.

A still further object of this invention is to provide circuit means which is remotely located away from the hand-piece unit and senses a low current electric signal and then in turn switches on higher levels of current that are required to operate various electrical devices such as linear solenoids, rotary solenoids, relays, electric motors and other electrical apparatus.

A still further object of this invention is to provide a modulated variable speed capability for air driven vane type motors or motors driven by any other mechanism through the use of an amplified low current electric signal.

A still further object of this invention is to provide a hand-piece assembly useful in dentistry which will eliminate the necessity for a separate water syringe.

Another object of this invention is to provide a light source means in the hand-piece unit of a power hand tool such as a dental device.

A further object of this invention is to provide a hand control system for dental hand-pieces which enables the manufacture of a completely portable dental drive system.

SUMMARY OF THE INVENTION

The hand control system for power hand tools as disclosed herein includes a manually operated control means for activating a low electric signal. Means is provided for actuating each operation of the power tool. Circuit means senses the low current electric signal when it is activated by the control means to provide a higher current operational signal to the tool actuating means. The manually operated control means may include manually electric switches or fluid switch means which are used to turn the low current electric signal on and off.

A particular feature of this invention is directed to the use of miniature electrical switches and variable electric resistive elements that are mounted on the hand-piece unit of a power hand tool. The switches are used in conjunction with solid state electronic circuitry which amplifies the low current electric signal and transmits a higher current operational signa to the tool actuating means.

Another feature of the invention is the use of electro-mechanical devices such as linear solenoids, rotary solenoids, relays, electric motors and other electrical apparatus which operates in response to the higher current operational signals transmitted from the circuit means. The electro-mechanical mechanisms in turn open and close hydraulic and pneumatic valves that regulate the flowing of fluids such as water and air to the hand-piece unit such as are used in dental drive assemblies.

A further feature of the invention is directed to the use of a potentiometer for providing a variable amount of current flow to the tool actuating means. The circuit means used in conjunction with the potentiometer includes a current regulating operational amplifier which senses the variable low current electric input signal and maintains a higher current operational signal that is proportional to the input signal. The actuating means includes an electro-mechanical mechanism for activating a variable speed operation of the power tool. In the case of a dental drive unit, the rotating tool members are capable of being driven at variable speeds.

Another feature of this invention is the particular configuration of a circuit means including means for amplifying a low current electric signal and switching means for receiving an current drive signal from the amplifying means and transmitting a higher level operational signal to the tool actuating means. The amplifier mechanism may comprise a servo amplifier which uses feedback to maintain the operational current signal proportional to the input signal where a variable resistance element is being used to control the variable speed of the tool member.

Another feature of the invention is directed to the use of a hand-piece unit having means for mounting a dental hand mirror thereon. The control mechanism is mounted on the hand-piece along with the dental hand mirror which may be removably mounted from the hand-piece unit. In this particular instance, the hand-piece unit is completely separate from the power tool itself. It is possible that a power tool may include a rotatable tool member mounted in a first hand-piece unit having a first finger-tip control mechanism while a second hand-piece unit is used to carry a second finger-tip control mechanism. In this type of configuration, a switch may be provided on the tool drive cabinet for engaging either the first or second hand-piece unit with an electrical current source.

Another feature of the invention is directed to the use of a light source means mounted on the hand-piece unit which carries a tool member. The light source means is used for dispensing light toward the tool member. This is particularly useful in a dental device having a rotatable tool member. A flexible bundle of optic fibers or fiber optic light source is used in a specific embodiment of this particular feature of the invention.

BRIEF DESCRIPTION OF DRAWINGS

Other objects of this invention will appear in the following description and appended claims, reference being made to the accompanying drawings forming a part of the specification wherein like reference characters designate corresponding parts in the several views.

DESCRIPTION OF SPECIFIC EMBODIMENTS

Figure 1:
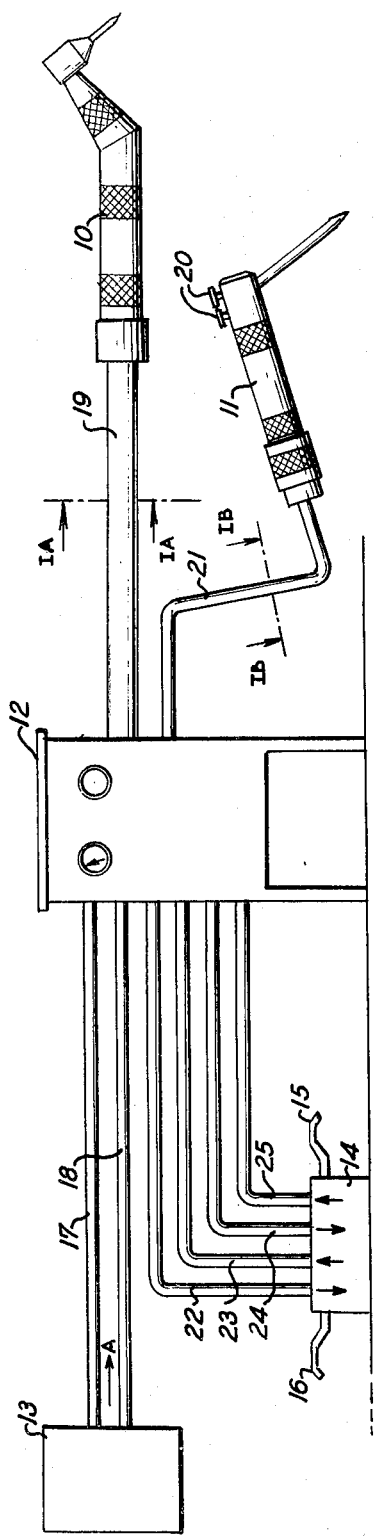
FIG. 1 is a schematic drawing of a conventional prior art dental drive assembly.

More specifically, reference being made to the drawings, one such conventional hand-piece assembly including a drill unit 10 and syringe unit 11 is shown in FIG. 1. An air and water supply 13 sends air and water in a direction as shown by the arrow A through the conduits 17 and 18, respectively. The air and water are sent through a dental control cabinet, generally designated 12, and are then directed through the foot controller 14 to the drill assembly 10 and/or the water syringe unit 11. Water and air move from the cabinet 12 to the drill unit 10 via conduit assembly 19, and to the syringe unit 11 via conduit assembly 21.

A foot-actuated control valve 14 is used to regulate the amount of air and/or water to be directed to the drill unit 10 and the buttons 20, which are miniature valves, regulate the amount of air and/or water to be directed to the syringe unit 11. Conduits 22 and 23 are used to carry air between the control cabinet 12 and the foot-actuated control valve 14 by depressing pedal 16, which regulates the cooling water to the hand-piece unit 10 by means of an air-operated water valve located within cabinet 12.

Conduits 24 and 25 are used to carry air between the control cabinet 12 and the foot-actuated control valve 14, by depressing pedal 15, which regulates the drive-air to the hand-piece unit 10 via conduit 19.

Conduit 21 is used to carry air and water from the control cabinet 12 to the control buttons 20 located on syringe unit 11. In the majority of cases, and as shown here, the syringe unit 11 is not controlled by the foot-actuated control valve 14, but by the control buttons 20.

Figure 2:
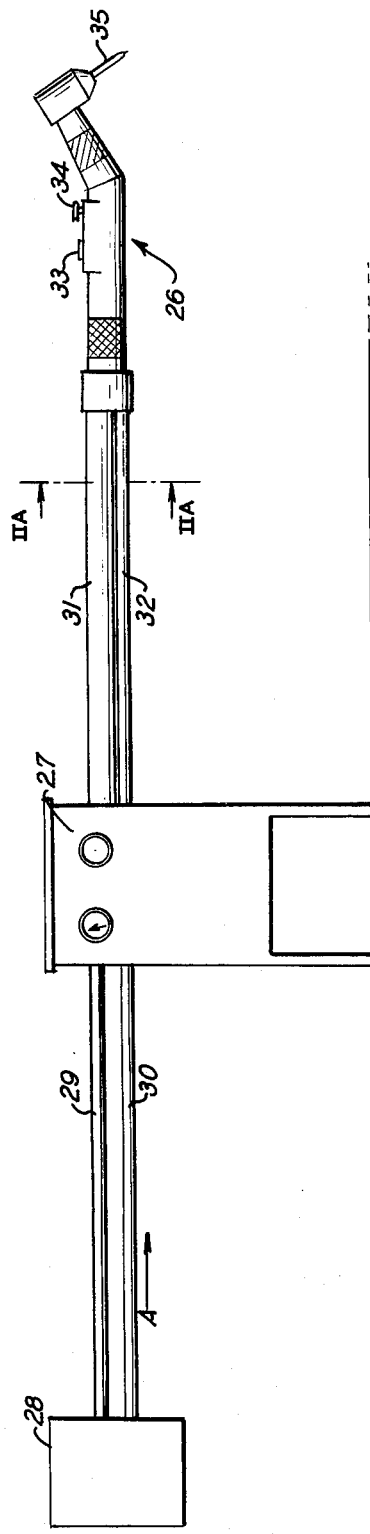
FIG. 2 is a schematic diagram of a dental drive system made in accordance with this invention.
Figure 1A:
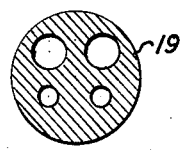
FIG. 1A is a cross-sectional view taken along line IA—IA of FIG. 1.
Figure 1B:
FIG. 1B is a cross-sectional view taken along line IB—IB of FIG. 1.
Figure 2A:
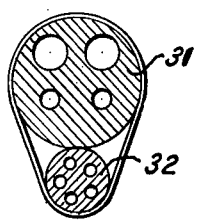
FIG. 2A is a cross-sectional view taken along line IIA—IIA of FIG. 2.
Figure 6A:
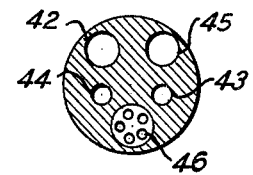
FIG. 6A is a cross-sectional view along line VIA—VIA of FIG. 6.

A hand control system made in accordance with this invention is shown in FIG. 2 and includes an air and water supply 28, a control cabinet 27, and a hand-piece unit 26. Air and water are conveyed through conduits 29 and 30 to the control cabinet 27 where conduit assembly 31 then conveys the air and water to the hand-piece unit 26, while electric conductor cable 32 is used to interconnect the electronics within cabinet 27 and control buttons 33 and 34 on hand-piece unit 26. The arrangement of conduits and electric cable assemblies are shown in FIGS. 2A and 6A. The syringe unit is integrally incorporated into the hand-piece unit 26 and eliminates the requirement for a separate hand-piece such as 11 in FIG. 1.

The control cabinet 12 also includes various types of components such as air and water filters, metering valves, gauges and related apparatus that provide the interconnection between the incoming supply of air and water, the foot-actuated control valve assembly 14 as shown in FIG. 1, and the hand-piece units 10 and 11. These same types of components are also found in the control cabinet 27 as shown in FIG. 2, except that there is no foot-actuated control valve, but rather, other types of electronic and electro-mechanical equipment.

While the specific embodiments of this disclosure are related to the field of dentistry, it is known that the same type of system may be incorporated in other types of medical units and power tools generally used in various other fields. Various types of tool members such as dental drills, surgical rotary files and saws, and other types of electro-mechanical devices may be controlled through the use of the hand control system of the present application.

Figure 3:
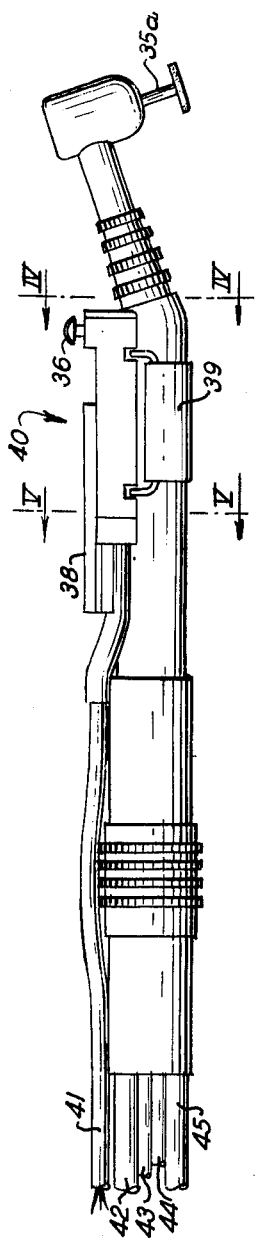
FIG. 3 is an elevational view of a manually operated control assembly made in accordance with this invention and mounted on a conventional dental drive hand-piece unit.

In FIG. 3, the linear potentiometer 38 provides control for variable amounts of very low current to an electronic module located in the dental drive cabinet 27 wherein a proportion of an amount of higher current is switched on to a rotary solenoid controlled valve. By sliding the potentiometer with the finger tip, the current to the rotary solenoid 68 (FIG. 10) is continuously variable from 0 current to the desired amount for opening the air valve that controls the speed of the air driven vane type motor on the hand-piece assembly 40. The potentiometer 38 can be either linear actuated as shown in FIG. 3 or rotary actuated as shown in FIG. 9 to accommodate various design requirements as discussed hereinabove.

In FIG. 2, the finger-tip control system as disclosed herein includes miniature electric switches 34 for turning the air and water on and off. A variable electric resistive element or linear potentiometer 33 is used in conjunction with solid state electronic circuitry for controlling the rotational speed of the tool member 35. Very low electric command current signals are held within the acceptable health-safety range of the dental and medical profession. These low current signals are sensed by a circuit means which provides a higher level operational current signal to the tool actuating mechanism.

When the switches 34 and the potentiometer 33 are hand manipulated, they switch on minute amounts of current on the order of about 10 micro amps. As indicated above, a potentiometer operates from the 0 current flow up to any desired amount that will operate an air valve. Thus, proportionately the low current electric signal will operate from 0 current flow to about 10 microamps as required to be maintained within the known health-safety range of the dental and medical profession. It is further well known that such low current electric signals are below the necessary current flow for operating a solenoid means. Thus, this low current electric signal is transmitted to an amplifier circuit which in turn switches on higher levels of current that are required to operate various types of electro-mechanical devices such as linear solenoids, rotary solenoids, relays, electric motors and the like. These electro-mechanical devices in turn open and close hydraulic and pneumatic valves that regulate the flow rate of fluids such as water and air to the hand-piece unit of the particular system. Various hand-piece units incorporating different modifications of the hand control system in accordance with this invention are shown in FIGS. 3 through 9B. More specifically, the hand control assembly, generally designated 40, includes a fastening strap assembly 39 which enables the control system of the invention to be adapted to existing hand-piece units. An externally mounted cable 41 is used to carry the low electric current signal controlled by the linear potentiometer 38 and the on-off switches 36 and 37. The electrical switch 37 is used to turn the chip-air on and off and switch 36 is used to turn the syringe water on and off. In these specific embodiments, the tool members 35a, 35b and 36c are rotated by variable speed air driven vane-type motors, the speed of which is regulated by the linear potentiometer 38. It is possible that the tool members 35a, 35b and 35c might also be driven by other means. The linear potentiometer 38 is used in conjunction with a current regulating operational amplifier which senses variable low current electric input signals and maintains a higher current operational signal that is proportional to the input signal, thus providing the control for the rotary solenoid valve which regulates the speed of the tool members 35a, 35b and 35c.

Several conduits are used to carry air and water to the dental hand-piece unit in each of the embodiments. The conduit 42 carries air to the air driven motor which rotates the tool members 35a, 35b and 35c. Conduit 43 carries chip-air to a location at the end of the hand-piece unit so that the work area may be cleared by a blast of air. The conduit 44 carries water which may be used in conjunction with cooling the rotating tool members 35a, 35b and 35c or used in the syringe mode when the electrical switch 36 is activated. The conduit 45 is an exhaust conduit. Each of the conduits 42, 43, 44 and 54 are commonly used in dental device systems and do not in and of themselves form a part of this invention.

Figure 9A:
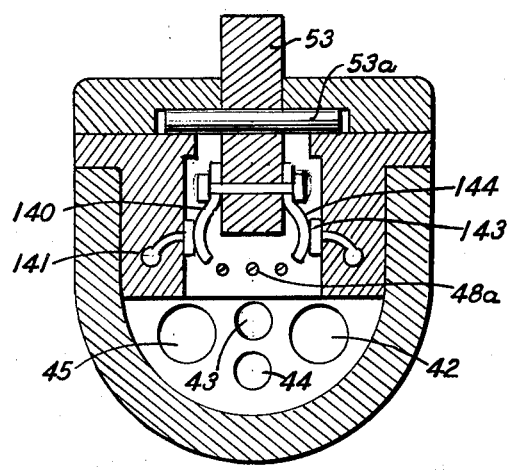
FIG. 9A is a cross-sectional view along line IXA—IXA of FIG. 9.
Figure 9B:
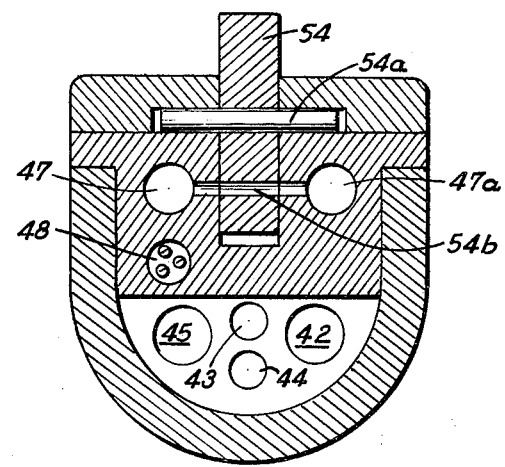
FIG. 9B is a cross-sectional view along line IXB—IXB of FIG. 9.
Figure 4:
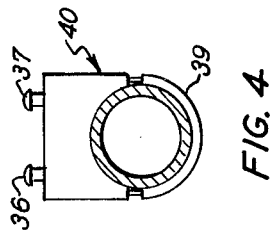
FIG. 4 is a cross-sectional view along line IV—IV of FIG. 3.
Figure 5:
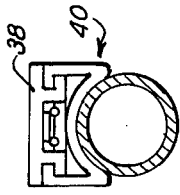
FIG. 5 is a cross-sectional view along line V—V of FIG. 3.
Figure 7:
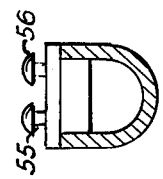
FIG. 7 is a cross-sectional view taken along line VII—VII of FIGS. 6 and 9.
Figure 8:
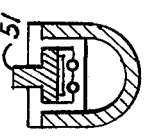
FIG. 8 is a cross-sectional view taken along line VIII—VIII of FIG. 6.
Figure 9:
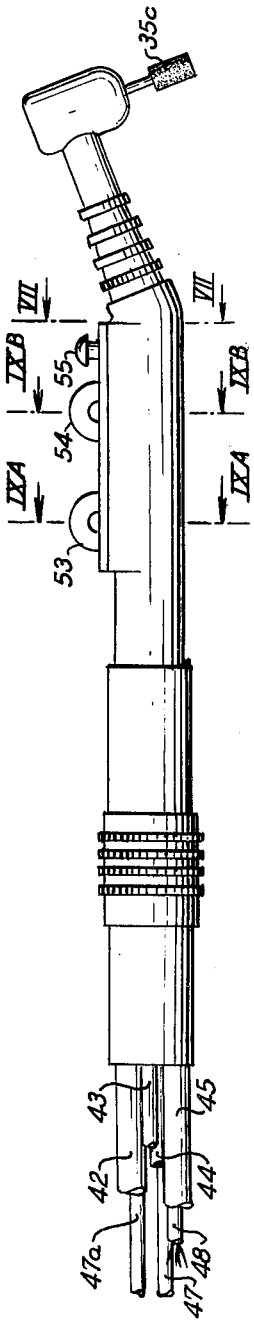
FIG. 9 is another embodiment of a dental drive hand-piece unit made in accordance with this invention.

Another embodiment of an assembly made in accordance with this invention is shown in FIGS. 9 and 9A and includes an internally routed cable 48 which carries the low current electric signal from switches 55 and 56 to the electro-mechanical mechanisms which control the chip-air and syringe water valves, and to the rotary potentiometer 53 which is used to provide variable control to the speed of the tool member 35c.

Figure 11:
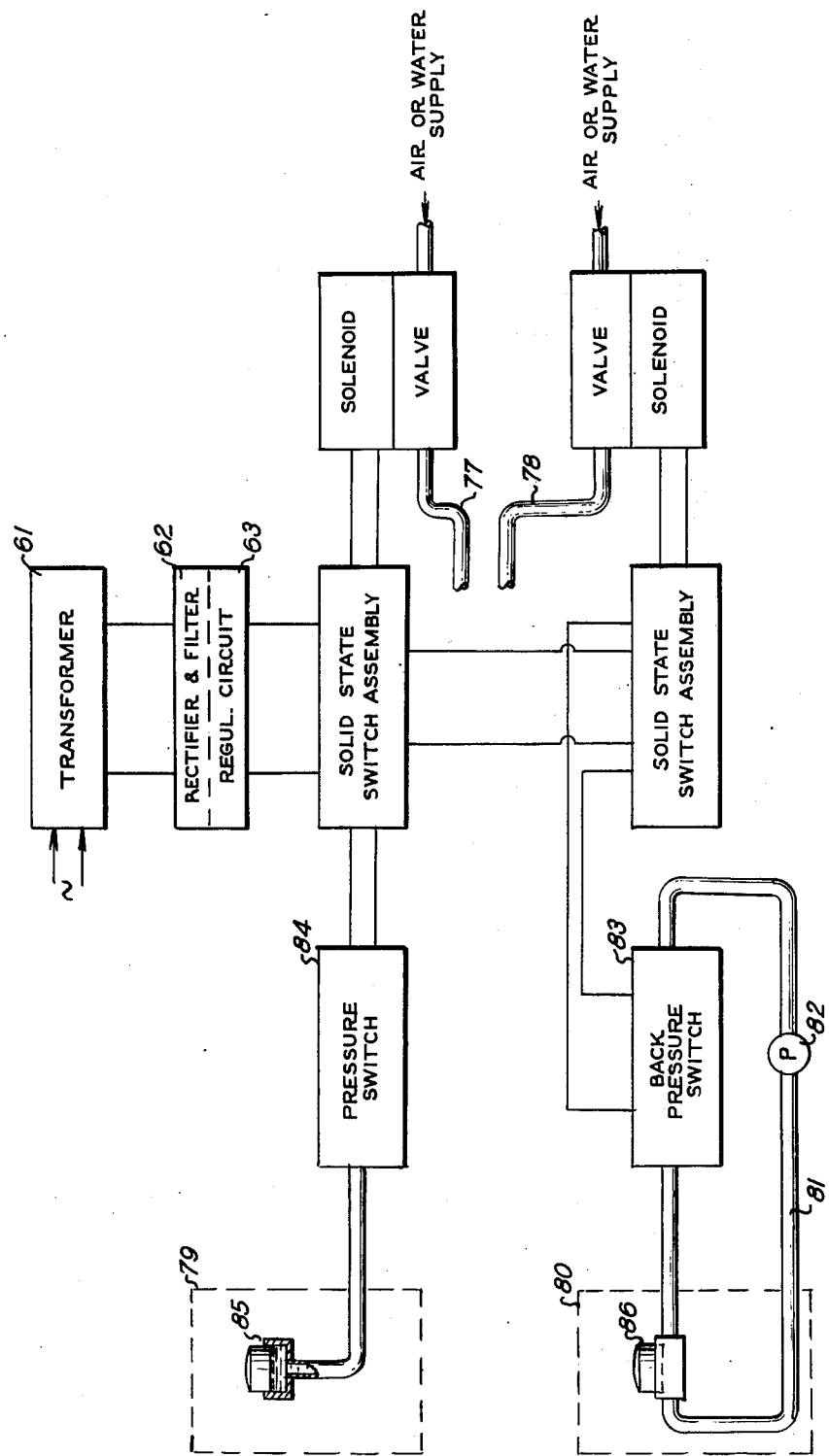
FIG. 11 is a schematic diagram showing two types of fluid finger-tip control assemblies used in a dental drive system made in accordance with this invention.

Another feature of the embodiment of FIG. 9 is shown in FIG. 9B. The difference between the feature of FIG. 9A and the feature of FIG. 9B is the speed control system for the vane type motor on the hand-piece unit. The thumb-control rotary potentiometer 53, as shown in the embodiment of FIG. 9A, requires two wires to provide the interconnect between the hand-piece unit and the electronics within the dental cabinet 27 which in turn regulates the speed of the tool member 35c. The thumbcontrol rotary wheel 54 of FIG. 9B is very similar to that of FIG. 9A except that the thumb wheel 54 is basically a miniature rotary valve in lieu of the rotary potentiometer 53 which acts as a back-pressure device which either controls an on-off switching system in the dental cabinet 27, or a variable speed control system for drive air, without the need for wires to the hand-piece unit. See control button 86 as shown in FIG. 11. Both types of controls shown in FIGS. 9A and 9B are used within the single embodiment of FIG. 9 for certain control systems. However, these controls 53 and 54 may be used separately. The on-off switches 55 and 56 in FIG. 7, and switches 36 and 37 in FIG. 4, all basically perform the same function of controlling chip-air or syringe water to the hand-piece unit, but are not limited to those specific functions alone.

Figure 6:
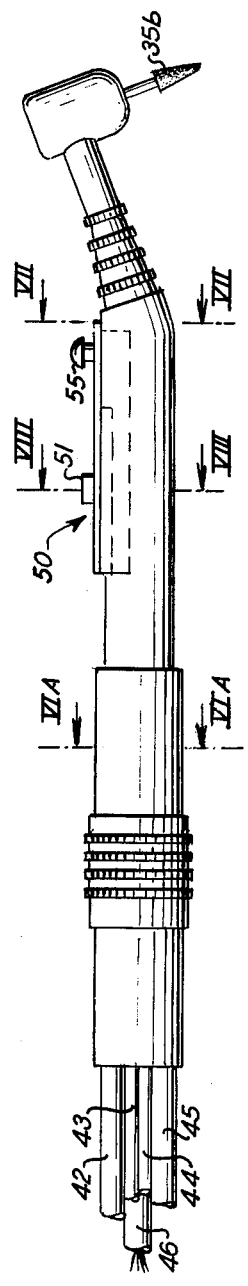
FIG. 6 is an elevational view of a dental drive hand-piece unit made in accordance with this invention.

A further embodiment of a hand-piece unit made in accordance with this invention is shown in FIG. 6 wherein the electrical cable 46 is located inside the unit. The hand control assembly 50 is integrally mounted as a part of the hand-piece unit and includes a linear potentiometer 51 and electrical on-off switches 55 and 56 which are used to turn chip-air and syringe water on and off.

Figure 10:
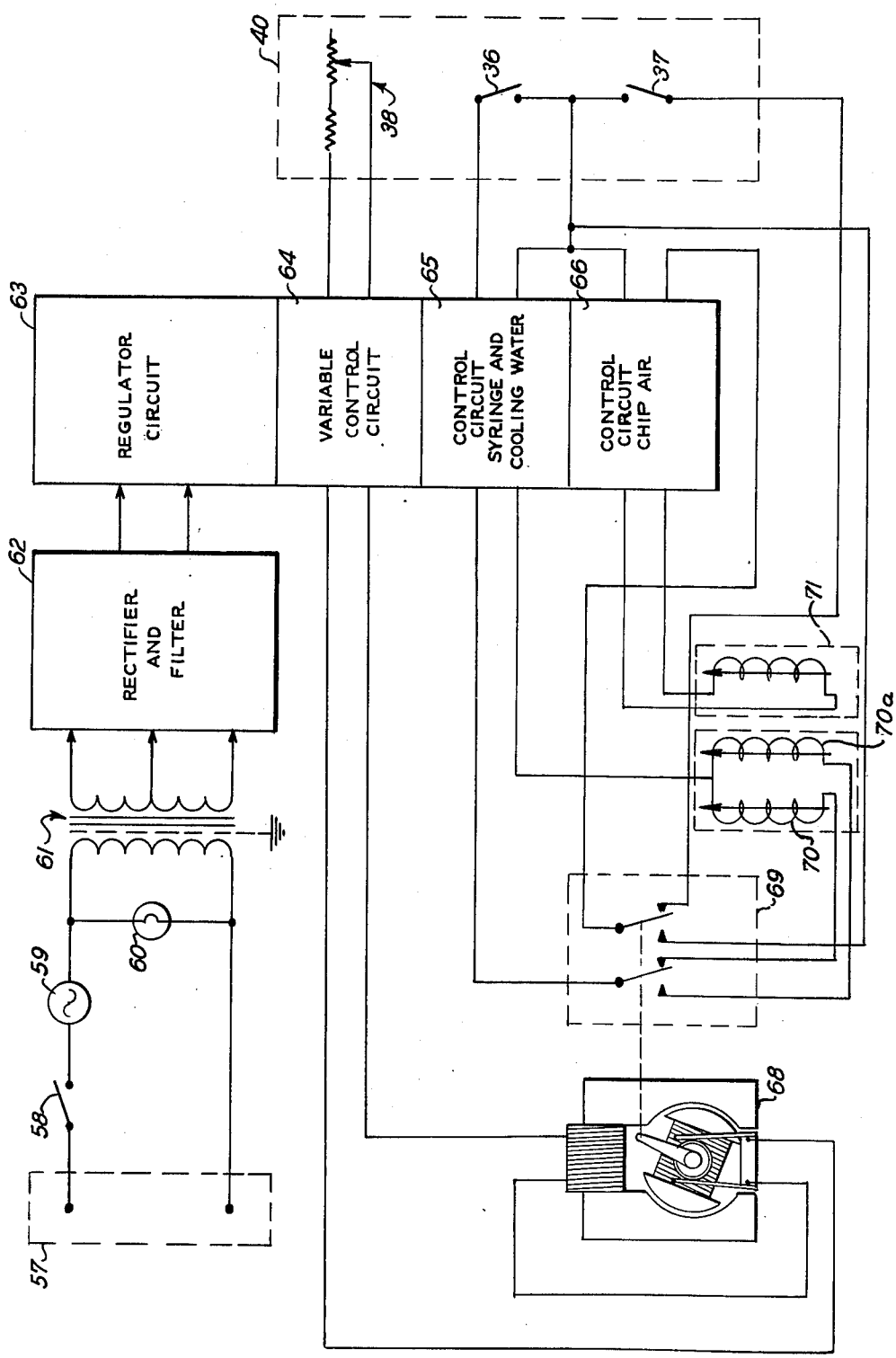
FIG. 10 is a schematic circuit diagram showing electronic control for a dental drive unit made in accordance with this invention.
Figure 10A:
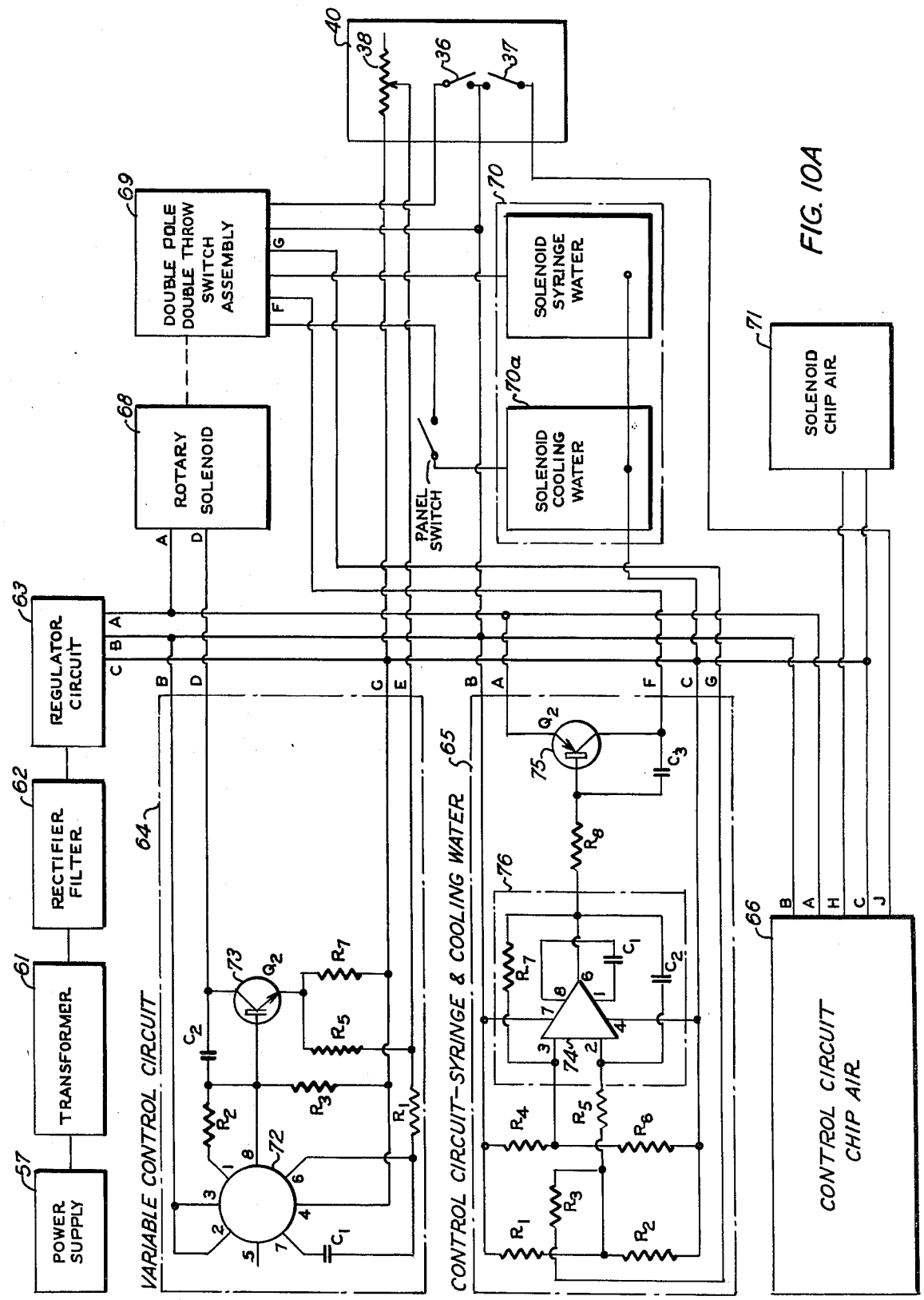
FIG. 10A is a more detailed illustration of the circuit diagram shown in FIG. 10.

Attention is now directed to FIGS. 10 and 10A which show the electronic system used to effectuate the desired results as set forth herein. A power supply 57 provides a 110 volt AC current. The switch 58 is used to turn the total system on and off. The fuse 59 protects the system and the lamp 60 is merely an indicating light showing that the system is operational.

An isolation step-down transformer 61 is used to produce an output voltage of 6.3 VAC either side of the center-tap. A rectifier and filter circuit 62 filters the signal from the transformer 61 to approximately 7.5 volts direct current. After the isolation transformer output has been rectified and filtered, it is regulated in the regulator circuit 63 to a low DC voltage in the range of from about 3 to 5 volts. Any standard rectifying and filtering circuit 62 and regulator circuit 63 may be used to effectuate the desired DC low voltage signal.

Figure 16:
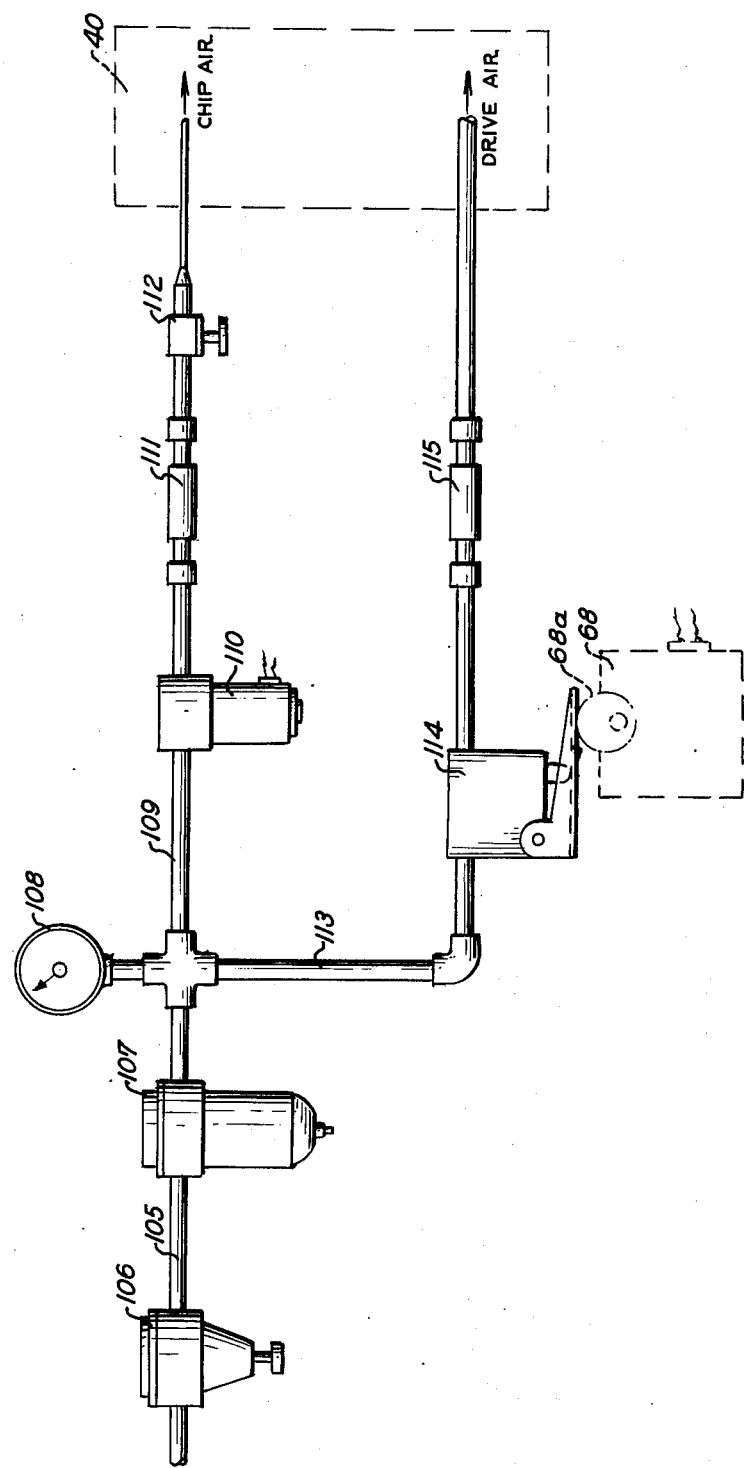
FIG. 16 is a schematic air flow diagram of an electronically controlled dental drive system made in accordance with this invention.

The higher current operational signal is transmitted via line A while the low electrical current command signal is provided via the line B as shown in FIG. 10A. The hand-piece assembly 40 includes the linear potentiometer 38 and on-off switches 36 and 37 which control the water and air, respectively. The potentiometer 38 works in conjunction with the variable control circuit 64 to operate the rotary solenoid 68 and double-pull, double-throw switch assembly 69. The on-off switch 36 works in conjunction with the control circuit 65 thereby turning the water on and off for the syringe and cooling operations. The control circuit 65 is interconnected with the solenoids 70 and 70a which open and close the respective water control valves. The switch 37 works in conjunction with the control circuit 66 to provide chip-air by activating the solenoid 71 which operates the air control valves that is an integral part of the solenoid assembly 110 as shown in FIG. 16.

The variable control circuit 64 is used to operate the rotary solenoid valve 68. The rotary solenoid valve 68 is a modulated valve which will supply a desired amount of air flow to create the desired turbine speed at the hand-piece unit thereby controlling the rotational speed of the tool members mounted therein. The linear potentiometer 38 is movable so that the resistance in the circuit may be changed over a range sufficient to cause the rotary solenoid 68 to go from a fully closed position to a fully open position. Furthermore, the rotary solenoid valve 68 may be operated in a continuously variable manner between these two extreme positions.

The operation of the variable control circuit is known basically as current regulation. The resistance of the potentiometer 38 is connected between pins C and E. This causes a small voltage change on the order of a few millivolts to appear at terminal 6 of the regulator 72. This small voltage shift is amplified and causes the base current for the switching means or transistor 73 to increase until sufficient current flows from terminal A through the rotary solenoid 68 into terminal B, through switching transistor 73 and then through the resistance $R_7$ to the common terminal C.

As disclosed the current flow from pin A through the rotary solenoid 68 and the terminal D through the transistor 73 and through the resistance $R_7$ produces a voltage drop across $R_7$ sufficient to cancel a few millivolts change applied at terminal 6 of the regulator 72. Consequently, this voltage drop will be maintained across the resistance $R_7$. If the 7.5 volts at pin A should increase or decrease due to changes in the rotary valve characteristics or due to any other change in supply, the amplifier or regulator 72 will alter the drive to the transistor 73 to maintain the precise desired current through the previously described circuit. Therefore, this variable control circuit 64 is a servo amplifier which uses feedback to maintain a higher level operational current that is proportional to the low current input signal provided by the linear potentiometer 38.

A control circuit 65 for the syringe and cooling water is identical to the control circuit 66 used for providing a supply of chip-air. The control circuits 65 and 66 are used to operate the solenoids 70, 70a and 71, respectively. The solenoids 70 and 70a operate water control valves and the solenoid 71 operates an air control valve as described hereinbelow. Upon closing the electrical switch 36, the very low current of about 10 micro amps is established across the pins B and G causing a potential on the terminal 2 of the amplifier 74 in the operational amplifier circuit 76. When this occurs, the output of the amplifier 74 at terminal 6 will go within a fraction of a volt to ground potential which is terminal C. This voltage of approximately one-half to 1 volt established at terminal 6 causes a current to flow out of the base of the transistor 75 through resistance $R_8$ which will limit the current to an appropriate value. The current flowing of the base of the transistor or switching means 75 is an amount sufficient to saturate the transistor 75 which has a switching current capability of up to 10 amps.

In this specific embodiment, the electro-mechanical solenoids 70, 70a and 71 operate at from 6 to 12 volts and thus the switching current is typically established at 1 to 2 amps. The 0.47 micro-farad capacitor C3 from collector to base at transistor Q2, has a Miller effect to prevent oscillation into terminal 2. The normal output at terminal 6 is near the +7.5 volts potential. When it goes from the high state to the low state, that is from the +7.5 volts to near ground voltage, some of this change in the voltage is fed as a current through capacitor C2, and back to the terminal 2 as negative feedback.

Positive feedback is applied from terminal 6 through resistance $R_7$ to terminal 3 of the operational amplifier 76. Basically, the resistors R1, R2, R4 and R6 form a bridge which maintains pin 2 slightly lower in voltage than pin 3. The output of the amplifier 74 will be positive at terminal 6 when the inverting input is more negative than the non-inverted input.

When the switches 36 and 37 located on the hand-piece unit are closed across B and G and B and J, the voltage combination now reverses the procedure whereby pin 3 will be more negative than pin 2 causing the output of the operational amplifier pin 6 to go to the low state. This switching action is applied to the transistor 75 which acts as a solid state switch to supply 7.5 volts to the solenoids 70, 70a and 71 connected to terminals F and C or H and C. In the case of the cooling water solenoid 70a as shown in FIG. 10A, a panel mounted on-off switch and/or the rotary solenoid override switch may inhibit the cooling water solenoid water activation.

As shown, the switching action at the hand-piece unit causes a minute current of about 10 micro amperes to create an offset voltage applied to the operational amplifier 76 with a gain of approximately 100,000. This will provide sufficient drive current signal to the transistor 75 acting as a DC switch to increase the voltage across the solenoid connection which is connected directly or indirectly at terminals F and C or H and C, respectively, as discussed hereinabove. When the switches 36 and 37 are released, the transistor 75 in the control circuits 65 and 66, respectively, blocks the current flow from terminal A through to terminal F or H thereby deactivating the solenoids 70, 70a and 71.

Further embodiments of the control assembly as disclosed herein are shown in FIG. 11. In the hand-piece unit 79, the finger-tip control means utilizes small amounts of fluid pressure such as liquid or gas pressures to switch on and off minute amounts of current through various solid state electronic switching modules located in the dental drive cabinet 27. Miniature pressure switch 84 is turned on and off by depressing the button 85 which changes the liquid or gaseous pressure acting on the pressure switch 84. The solid state switching assembly is activated by the pressure switch 84 thereby switching on higher levels of current to perform the appropriate function as represented by the solenoid valve turning on an air or water supply through conduit 77 which exists to the hand-piece unit 79.

The hand-piece unit 80 works in conjunction with a back pressure switch 83 which is turned on and off by the finger-tip control valve 86 located on the hand-piece unit 80. In this embodiment, the fluid medium such as gas or liquid is conveyed through the conduit 81 by pump 82. By pressing the valve 86, or by rotating the thumb-wheel valve as shown in FIG. 9B, small amounts of varying pressure are sensed by the back pressure switch which in turn activates the solid state switching assembly connected thereto. The associated solenoid valve is then activated to send air or water via conduit 78 back to the hand-piece unit 80.

The difference between the embodiments as shown in FIG. 11 as compared to the earlier embodiments is that miniature finger-tip fluid controls are located on the hand-piece instead of miniature electric switches. While the electrical switches utilize low current switching signals at the hand-piece unit, the embodiments of FIG. 11 either produce or control small amounts of varying pressures or regulate line pressure of fluids to activate pressure switches which in turn actuate associated solid state switching assemblies located in the dental cabinet 27.

Figure 12:
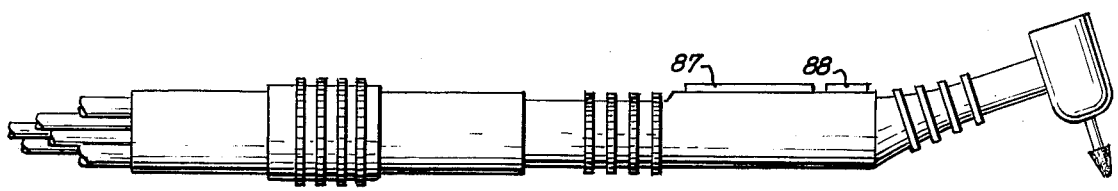
FIG. 12 is a side elevational view of a further modification of a dental drive hand-piece unit made in accordance with this invention.
Figure 13:
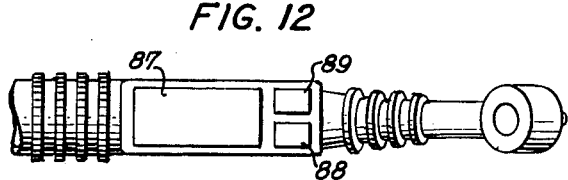
FIG. 13 is a top plan view of the unit shown in FIG. 12.
Figure 14:
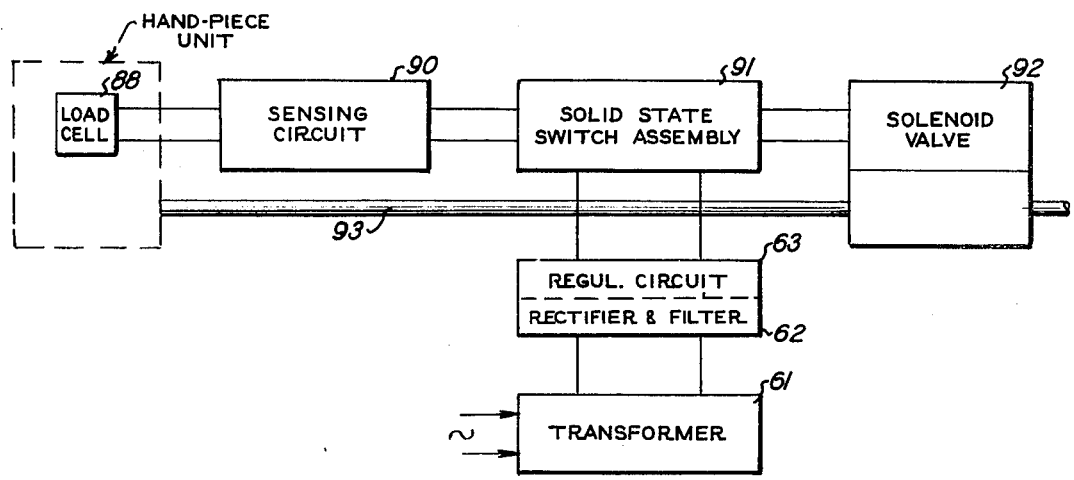
FIG. 14 is a schematic circuit diagram for the finger-tip control system as shown on the unit of FIGS. 12 and 13.

A further embodiment is shown in FIGS. 12 through 14 wherein the finger-tip control mechanism utilizes miniature pressure transducers and/or load cells 87, 88 and 89. The load cell 87 may be used to limit sensitivity for variable control of the low current electric signal. A typical signal system function is schematically shown in FIG. 14 wherein a load cell 88 is mounted on the hand-piece unit and activates the sensing circuit 90 which in turn actuates the solid state switching assembly 91. The solenoid 92 controls a water or air supply valve for sending the requisite supply to the hand-piece via conduit 93. The sensing circuit 90 and solid state switching assembly 91 are the same type units which were used in the first embodiment described hereinabove. Furthermore, this embodiment uses the same transformer 61 and rectifying-filtering circuit 62 and regulating circuit 63 as used in the embodiment described hereinabove. This particular embodiment eliminates all moving parts on the control assembly of the hand-piece unit except for a simple spring return mechanism to apply varying pressures on cell 87 to control drill speeds.

Figure 15:
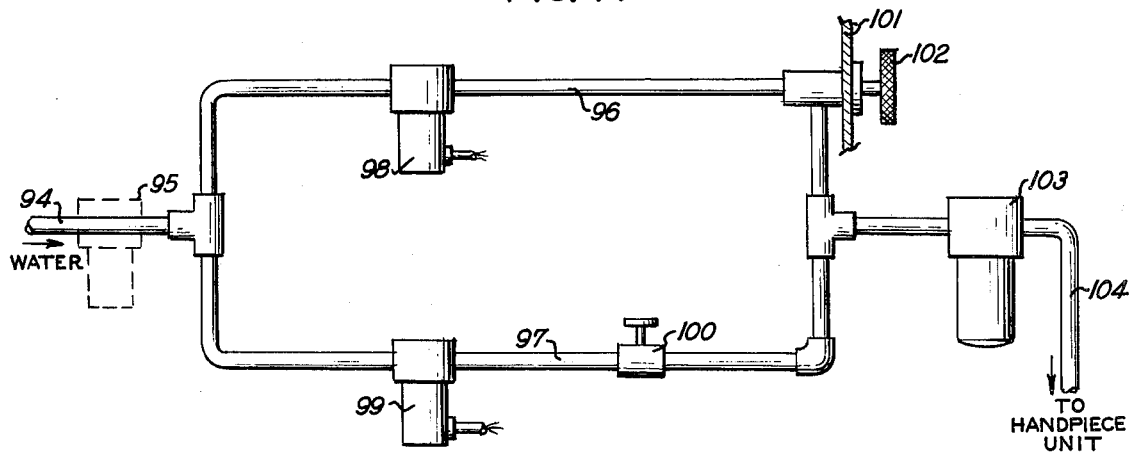
FIG. 15 is a water flow diagram used in the electronically controlled dental drive unit system made in accordance with this invention.

The schematic diagram of FIG. 15 shows the manner in which water may be supplied to the hand-piece unit. Water comes into the conduit 94 and may be optionally filtered by the filter 95. The control knob 102 mounted in the panel 101 of the cabinet 27 controls the amount of flow of cooling water through the conduit 96. A switch on the hand-piece unit turns the flow on and off by way of the solenoid control valve 98. The cooling water goes to the hand-piece assembly via the filter 103 and conduit 104 to maintain cooling at the tip of the rotating tool member. Syringe water is controlled by the metering valve 100 as it flows through the conduit 97. Any type of switch as discussed herein as located on the hand-piece unit will control the flow of syringe water by way of the solenoid actuated valve 99.

A schematic diagram of air flow in a dental drive system unit made in accordance with this invention is shown in FIG. 16. Air comes into the conduit 105 which includes an air pressure regulator 106 and a primary air filter 107. Air pressure gauge 108 is used to determine the line pressure in the system. Chip-air is directed through conduit 109 and may be adjusted by way of the adjusting screw 112 and filtered by line filter 111 before it is used at the hand-piece unit 40. Electric solenoid valve 110 is turned on and off by a switch located on the hand-piece unit 40 as described hereinabove. The drive air for the variable speed air driven motor is directed through conduit 113 and filtered by filter 115 located therein. The rotary solenoid 68 controls the air metering valve 114 which is operated by cam 68a affixed to the rotary solenoid shaft. This relationship between the rotary solenoid 68 and the air metering valve 114 provides the variable amounts of drive air to control the speed of the rotating tool member mounted in the hand-piece unit 40.

Figure 17:
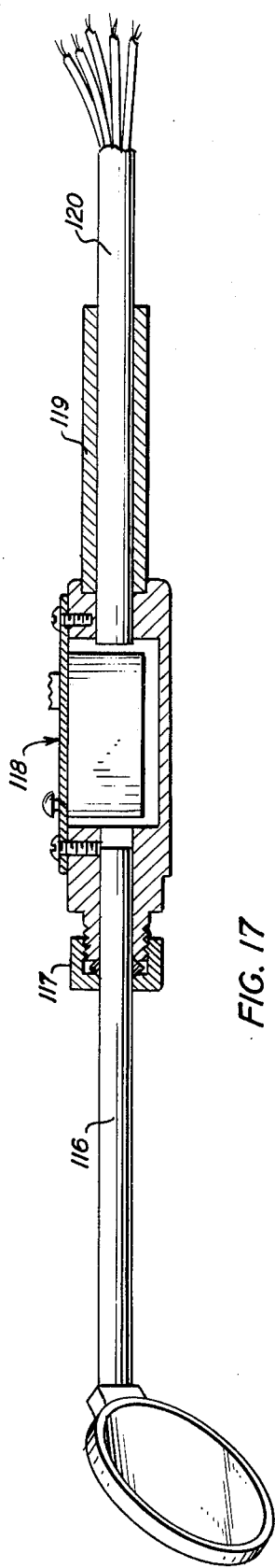
FIG. 17 is a cross-sectional view of a manually operated mirror mounted control assembly made in accordance with this invention.

A further embodiment of a hand control system made in accordance with this invention is shown in FIG. 17. This embodiment incorporates the same basic type of switching and modulated variable speed control mechanisms that have been described hereinabove. In this instance, however, the finger-tip control assembly is used in conjunction with a dental mirror. This embodiment offers several features which will allow the operator to manipulate the tool member such as the drill in one hand with 100 percent freedom of position. That is, there are no restrictions due to the finger positions on the hand-piece unit with respect to manipulating on-off switches. The finger-tip capability of controlling the speed of the drill, and turning chip-air and syringe water on or off may be effected with the other hand.

The dental mirror 116 is disposed in a friction collar 117 with the control mechanism 118 being mounted on a handle 119 and controlling electric current through the cable 120 which is basically the same as cable 46 in FIG. 6. The operator may choose to remove the dental mirror 117 from the hand-piece unit and use the switch 118 by itself. This allows the operator to use both hands with any freedom of position he chooses when there is no need for a mirror. In some special cases, it is possible that the dental or medical assistant can operate the switch assembly to assist in the control functions of the hand-piece unit if so directed by the dentist or surgeon. This would be an excellent aid in training and instruction.

A further feature of the embodiment of FIG. 17 is that the hand-piece unit is completely separated from the power tool. The rotatable tool member may be mounted in a first hand-piece unit having a first finger-tip control mechanism. A second hand-piece unit separate from the first hand-piece unit has a second finger-tip control mechanism. The circuit means may include a panel mounted switch for engaging either the first or second hand-piece unit with an electrical current source as desired. Thus, there is a requirement for only one electronic control system within the dental cabinet for either of the hand-piece units.

Figure 19:
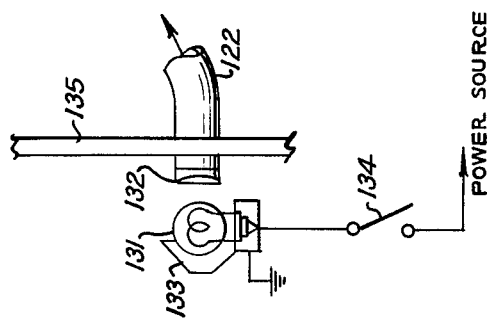
FIG. 19 is a schematic diagram of a light source assembly used in conjunction with the hand-piece unit as shown in FIG. 18.
Figure 18:
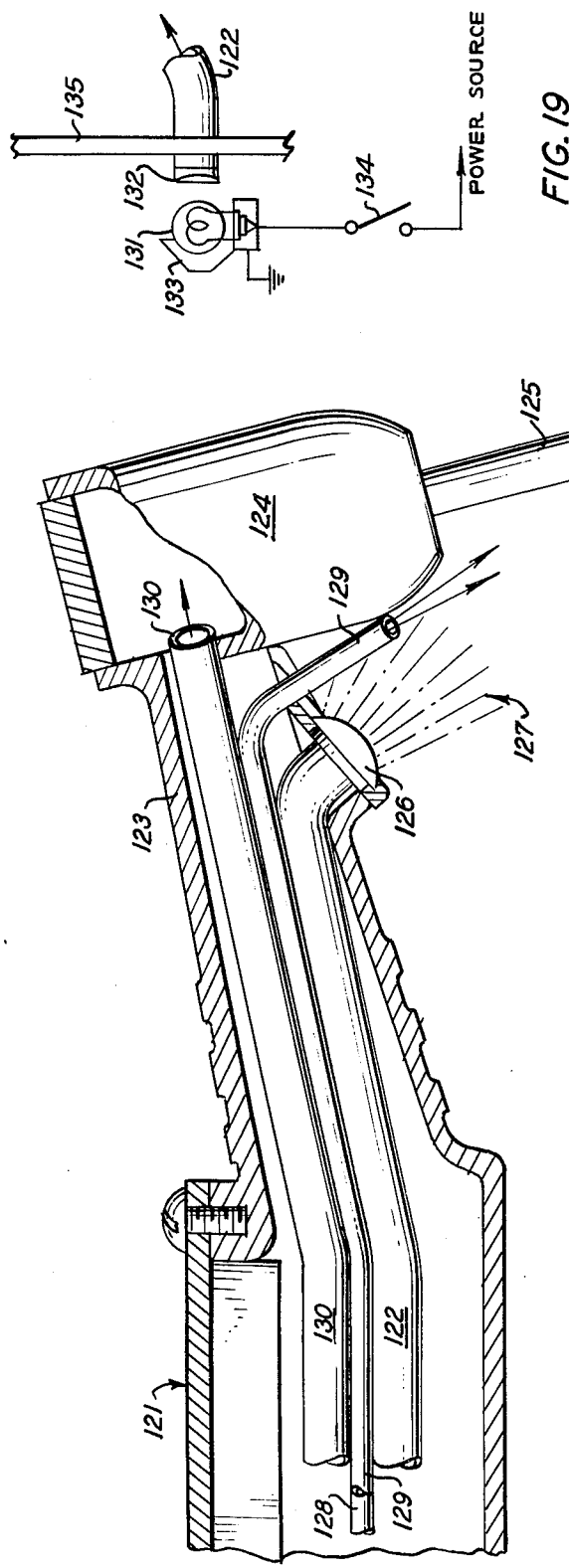
FIG. 18 is a cross-sectional view of a dental hand-piece unit having a light source means mounted therein in accordance with this invention.

Another embodiment of a dental system made in accordance with this invention is shown in FIGS. 18 and 19. In this embodiment, the power tool is a dental drill which includes a tool member 125 mounted in the head 124 of the hand-piece unit 123. A source of light 127 is mounted on the hand-piece unit 123 for dispersing light towards the tool member 125. In this embodiment, the light source mechanism includes a fiber-optics bundle 122 that is mounted in the hand-piece unit 123. A finger-tip control switch assembly 121 may include an additional switch for turning the light source on and off.

A condensing lens 132 is located at one end of the fiber-optics bundle 122 inside of the dental cabinet 135. A lamp 131 used in conjunction with reflector 133 is focused into the fiber-optics bundle 122 when switched on at the panel by switch 134 or a finger-tip control switch mounted on assembly 121. The path of light is then directed through that bundle 122 and a dispersing lens 126 mounted in the hand-piece unit 123.

The light source embodiment allows the operator to perform difficult operations in areas where he would normally have to reflect light off of a mirror such as a dental mirror. This light source means may be used in combination with any of the aforementioned operations. The drive air is directed through the conduit 130 to operate the air driven motor. Water used for cooling or as syringe water is carried by conduit 128 and chip-air is carried by conduit 129.

While all of the embodiments have been described with respect to a dental drive assembly, it is clear that the hand control system as disclosed herein may be used in many different types of professional equipment and is therefore not limited to simply the dental profession.

Further features of the invention in accordance with this invention are shown in FIGS. 9A and 9B. The rotary potentiometer wheel 53 is mounted on shaft 53a as an integral part of the hand-piece assembly as shown in FIG. 9. Wiper elements 140 and 144 are mounted on the rotatably mounted wheel 53 in a manner as shown. The wiper element 140 contacts the rotary potentiometer winding 141 on one side of the wheel 53. The wiper element 144 is used in conjunction with the contact plate 43 which is connected to the potentiometer wire. The wiper elements 140 and 144 function in the same manner as the movable element 38 as shown in the embodiment of FIG. 3. The purpose of the rotary element 53 is to vary the amount of resistance in the circuit as shown in FIG. 10.

The thumb wheel 54 shown in FIG. 9B illustrates a rotary valve mounted on a shaft 54a as an integral part of the hand assembly. The wheel 54 is circular and includes an opening 54b while is annular and extends only a partial distance along the circumference of the wheel 54. Ducts (not numbered) lead from the conduits 47 and 47a to the wheel 54. These ducts also have an annular shape while extends for a distance adjacent the circumference and matches the shape of the opening 54b. Thus, as the wheel turns, the passage through the wheel opening 54b is controlled. That is, control air comes into the device via the conduit 47 and passes out of the device through conduit 47a. The turning of the thumb wheel 54 will effect an open passage between the conduits 47 and 47a through the opening 54b when the opening 54b is in alignment with the ducts (not numbered) leading from the conduits 47 and 47a. This type of rotary valve may be effective to accomplish the results achieved by the control member 86 as shown in FIG. 11.

Both of the devices constitute a means for controlling the drive air portion of the hand assembly. However, these devices are not to be limited to the drive air control alone. In each of the FIGS. 9A and 9B, the drive air passes through conduit 42 and the exhaust air passes through conduit 45. The chip-air passes through conduit 43 and water passes through conduit 44. The water may be used for cooling in mode 1 and as syringe water in mode 2.

ADVANTAGES OF THE INVENTION

There are numerous advantages associated with the hand control system as disclosed herein. Many have already been discussed hereinabove. In the area of dentistry, the water syringe hand-piece assembly is completely eliminated. The drill cooling water supply is turned on automatically when the air driven vane type motor is turned on for rotating the tool member. In the hand finger-tip control system of the present invention, the cooling water may be converted from the metered portion of the system and directed into the syringe when desired by the operator. This is accomplished by placing a miniature switch on the hand-piece unit as disclosed hereinabove to divert the cooling water for use as syringe water.

The electronic system as disclosed herein provides low level command currents at the hand-piece assembly which are within the health and safety levels of the dental and medical profession. It is impossible for higher levels of current to ever reach the hand-piece assembly. Furthermore, electrical short circuits or breakdowns in the modules located within the cabinet or the hand-piece itself cannot, in any way, present a health hazzard problem or endanger the lives of the patient or laboratory specimen.

It is also possible that a complete dental and/or medical drive system can be readily adapted to a portable unit. Such a portable unit may be used for in-patients who are confined to convalescent, nursing homes and the like and cannot be transported into dental or medical offices because of their physical condition. Such a complete portable system may also be used in dental and medical training situations.

The elimination of the foot-actuated control valve allows the operator to adjust his body to the most desirable working position without being restricted by the position of the foot-actuated control valve assembly. By eliminating the foot-actuated control and placing the control on the hand-piece unit itself, water and air can be modulated and/or controlled more accurately and with more sensitivity. It requires only light finger-tip pressures and manipulations to control the flow of water and air to the hand-piece unit.

While the hand control system for power hand tools has been shown and described in detail, it is obvious that this invention is not to be considered as being limited to the exact form disclosed, and that changes in detail and construction may be made wherein the scope of the invention, without departing from the spirit thereof.

Having thus set forth and disclosed the nature of this invention, what is claimed is:

1. A hand control system for power hand tools comprising:
    a. means for actuating an operation of the power hand tool,
    b. manually operated control means for activating a low current electric command signal maintained at up to about 10 micro amps and below the necessary current flow for operating said actuating means,
    c. said command signal electrically flowing through said manually operated control means,
    d. circuit means separate from the manually operated control means and including amplifying means for providing a higher current operational signal to said tool operation actuating means,
    e. said amplifying means being responsive to the low current electric command signal when said command signal is activated by said control means to cause said higher current operational signal to operate said tool actuating means.

2. A system as defined in claim 1 wherein said control means includes manually operated electric switch means which turns the low current electric command signal on and off.

3. A system as defined in claim 1 wherein said control means includes fluid switch means for providing controlled pressure changes and means for sensing said pressure changes to turn said low current electric command signal on and off.

4. A system as defined in claim 3 wherein said fluid switch means comprises a pressure switch and a miniature pressure plunger assembly for controlling the pressure switch.

5. A system as defined in claim 3 wherein said fluid switch means comprises a back-pressure switch and a finger-tip actuated flow-metering valve.

6. A system as defined in claim 1 wherein said control means includes an electric pressure transducer and means for sensing a change in finger-tip pressure on said transducer to turn said low current electric command signal on and off.

7. A system as defined in claim 1 wherein said low current electric command signal is provided by a direct current supply means.

8. A system as defined in claim 7 wherein said direct current supply means includes a transformer, rectifying means and regulating means.

9. A system as defined in claim 1 wherein said circuit means includes switching means for receiving an amplified current drive signal from said amplifying means and transmitting said higher current operational signal to said actuating means.

10. A system as defined in claim 9 wherein said switching means prevents current flow when said manually operated control means is released thereby deactivating said actuating means.

11. A system as defined in claim 9 wherein said amplifying means includes an operational amplifier having a current gain sufficient to provide an amplified current drive signal to said switching means.

12. A system as defined in claim 1 wherein said switching means includes a transistor and said operational amplifier has a current gain of about 100,000.

13. A system as defined in claim 1 wherein said actuating means includes an electro-mechanical mechanism for activating the operation of the tool member of said power tool.

14. A system as defined in claim 13 wherein said tool member is operated with an air driven motor and said electro-mechanical mechanism includes a control valve to supply air to the air driven motor and a solenoid for opening and closing said air control valve.

15. A system as defined in claim 1 wherein said control means includes a potentiometer for providing a variable low current electric command signal to said actuating means.

16. A system as defined in claim 1 wherein said control means includes a potentiometer having a variable resistance for providing a variable low current electric command signal, said amplifying means includes a current regulating operational amplifier which is responsive to said variable low current electric command signal and maintains a higher current operational signal that is proportional to said command signal, and said actuating means includes an electro-mechanical mechanism for activating a variable speed operation of the power tool.

17. A system as defined in claim 16 wherein
said electro-mechanical mechanism includes a rotary solenoid and
said circuit means includes a switching means for receiving the higher current operational signal and transmitting said current operational signal to the rotary solenoid.

18. A control assembly as defined in claim 1 wherein
said power tool includes a tool member mounted in said hand-piece unit and
a light source means is mounted on the hand-piece unit for dispersing light toward the tool member.

19. A control assembly as defined in claim 18 wherein
the power tool is a dental device having a rotatable tool member.

20. A control assembly as defined in claim 19 wherein
said light source means includes a fiber-optic bundle mounted in the hand-piece unit and lens means for dispersing light transmitted by the fiber-optic bundle.

21. A system as defined in claim 1 wherein
said control means includes an isolation transformer, rectifying means and regulating means for providing said low current electric signal.

22. A system as defined in claim 1 wherein
said actuating means includes an electro-mechanical mechanism for actuating said power tool.

23. A system as defined in claim 22 wherein
said power tool is operated with an air driven motor and
said electro-mechanical mechanism includes a control valve to supply air to the air driven motor and a solenoid for opening and closing said air control valve.

24. In a power tool having a hand-piece unit, a control assembly comprising:
a. means for actuating an operation of the power tool,
b. finger-tip control means located on the hand-piece unit for activating a low current electric input signal maintained at up to about 10 micro amps and below the necessary current flow for operating said actuating means,
c. said input signal electrically flowing through said manually operated control means,
d. circuits means separate from the manually operated control means and including amplifying means for providing a higher current operational signal to said tool operation actuating means,
e. said amplifying means being responsive to the low current electric command signal when said command signal is activated by said control means to cause said higher current operational signal to operate said tool actuating means.

25. A control assembly as defined in claim 24 wherein
said power tool includes a rotatable tool member mounted in said hand-piece unit and an air driven motor for rotating said tool member,
said finger-tip control means includes a variable electric resistive element providing a variable low current input signal for controlling the rotational speed of the tool member, and
said circuit means includes switching means for receiving an amplified current drive signal from said amplifying means and transmitting said higher current operational signal to said air driven motor.

26. A control assembly as defined in claim 24 wherein
said power tool includes a rotatable tool member and an air driven motor for rotating said tool member,
said control means includes a potentiometer having a variable resistance for providing a variable low current electric input signal, and
said amplifying means includes an amplifier means which is responsive to said variable low current input signal and maintains a higher current operational signal that is proportional to said low current input signal provided by the linear potentiometer.

27. A control assembly as defined in claim 26 wherein
said amplifier means comprises a servo amplifier which uses feedback to maintain the higher current operational signal proportional to the variable low current input signal.

28. A control assembly as defined in claim 24 wherein
said power tool is a dental device having an air driven motor for tool members rotatably mounted in said hand-piece unit, means for providing cooling water to the rotating tool members and means for providing syringe water.

29. A control assembly as defined in claim 28 wherein
said actuating means includes means for operating said air driven motor, means for operating said cooling water means and means for operating said syringe water means,
said circuit means includes switching means for receiving an amplified current drive signal from said amplifying means and transmitting said higher current operational signal to each said operating means.

30. A control assembly as defined in claim 28 wherein
said actuating means includes means for operating said air driven motor, means for operating said cooling water means and means for operating said syringe water means,
said amplifying means comprises first amplifying and switching means for providing said higher current operational signal to the operating means for said air driven motor, second amplifying and switching means for providing said higher current operational signal to the operating means for said cooling motor, and third amplifying and switching means for providing said higher current operational signal to the operating means for the syringe water.

31. A control assembly as defined in claim 30 wherein
said finger-tip control means includes a potentiometer having a variable resistance for providing a variable low current electric input signal,
said first amplifying and switching means includes means for sensing said variable low current input signal and maintaining a higher current operational signal that is proportional to said variable low current input signal provided by the potentiometer.

32. A control assembly as defined in claim 30 wherein each said switching means prevents current flow when said finger-tip control means is released thereby deactivating said actuating means.

33. A control assembly as defined in claim 30 wherein
each said amplifying means includes an operational amplifier having a current gain sufficient to provide a current drive signal to each said switching means.

34. A control assembly as defined in claim 30 wherein
said finger-tip control means includes a variable electric resistive element providing a variable low current electric input signal for controlling the rotational speed of the tool member and
said first amplifying means includes means for sensing said variable low current input signal and maintaining a higher current operational signal that is proportional to said variable low current input signal provided by the variable electric resistive element.

35. A control assembly as defined in claim 28 wherein
said tool actuating means includes an electro-mechanical mechanism for operating each said operation of the dental device and air control valve means for controlling an air supply to the air driven motor and first water control valve means for controlling the flow of cooling water and second water control valve means for controlling the flow of syringe water.

36. A control assembly as defined in claim 35 wherein
said electro-mechanical mechanism includes a solenoid means for controlling the air control valve means and the first and second water control valve means.

37. A control assembly as defined in claim 36 wherein
said air control valve means is a variable air control valve and
said solenoid means includes a rotary solenoid for adjusting said variable air control valve,
said finger-tip control means includes a potentiometer having a variable resistance and
said amplifying means includes an amplifier means which is responsive to said low current electric input signal and maintains a higher current operational signal that is proportional to said low current input signal provided by the potentiometer.

38. A control assembly as defined in claim 28 wherein
said dental device includes a light source means mounted on the hand-piece unit and
said finger-tip control means includes a manually operated switch which turns a low current electric signal on and off thereby turning a higher current operational signal on and off with respect to the light source means.

39. A control assembly as defined in claim 38 wherein
said light source means includes a fiber-optic bundle mounted in the hand-piece unit and lens means for dispersing light transmitted by the fiber-optic bundle.

40. A control assembly as defined in claim 24 wherein
said hand-piece unit includes means for mounting a dental hand mirror.

41. A control assembly as defined in claim 24 wherein
said hand-piece unit is completely separated from the power tool.

42. A control assembly as defined in claim 24 wherein
said power tool includes a rotatable tool member mounted in a first hand-piece unit having a first finger-tip control mechanism and a second hand-piece unit having a second finger-tip control mechanism.

43. A control assembly as defined in claim 42 wherein
said circuit means includes a switch for engaging one of said first and second hand-piece units with a low current electric source.

44. A hand control system for power hand tools comprising:
a. means for actuating an operation of the power hand tool,
b. manually operated control means for activating a low current electric command signal maintained below the necessary current flow for operating a solenoid means,
c. said command signal electrically flowing through said manually operated control means,
d. circuit means separate from the manually operated control means including amplifying means for providing a higher current operational signal to said tool operation actuating means,
e. said amplifying means being responsive to the low current electric command signal when said command signal is activated by said control means to cause said higher current operational signal to operate said tool actuating means.

45. A system as defined in claim 44, wherein
said control means includes manually operated electric switch means which turns the low current electric signal on and off.

46. A system as defined in claim 44, wherein
said control means includes fluid switch means for providing controlled pressure changes and means for sensing said pressure changes to turn said low current electric signal on and off.

47. A system as defined in claim 46 wherein
said fluid switch means comprises a pressure switch and a minature pressure plunger assembly for controlling the pressure switch.

48. A system as defined in claim 46 wherein
said fluid switch means comprises a back-pressure switch and a finger-tip actuated flow-metering valve.

49. A system as defined in claim 44 wherein
said control means includes an electric pressure transducer and means for sensing a change in finger-tip pressure on said transducer to turn said low current electric signal on and off.

50. A system as defined in claim 44 wherein
said low current electric signal is provided by a direct current supply means.

51. A system as defined in claim 50 wherein
said direct current supply means includes a transformer, rectifying means and regulating means.

52. A system as defined in claim 44 wherein
said circuit means includes switching means for receiving an amplified current drive signal from said amplifying means and transmitting said higher current operational signal to said actuating means.

53. A system as defined in claim 52 wherein said switching means prevents current flow when said manually operated control means is released thereby deactivating said actuating means.

54. A system as defined in claim 52 wherein said amplifying means includes an operational amplifier having a current gain sufficient to provide a current drive signal to said switching means.

55. A system as defined in claim 54 wherein said switching means includes a transistor and said operational amplifier has a current gain of about 100,000.

56. A system as defined in claim 44 wherein said control means includes a potentiometer for providing a variable amount of current flow to said actuating means.

57. A system as defined in claim 44 wherein said control means includes a potentiometer having a variable resistance for providing a variable low current electric input signal, said amplifying means includes a current regulating operational amplifyer which is responsive to said variable low current electric input signal and maintains a higher current operational signal that is proportional to said input signal, and said actuating means includes an electro-mechanical mechanism for activating a variable speed operation of the power tool.

58. A system as defined in claim 57 wherein said electro-mechanical mechanism includes a rotary solenoid and said circuit means includes a switching means for receiving the higher current operational signal and transmitting said current operational signal to the rotary solenoid.

59. In a power tool having a hand-piece unit, a control assembly comprising:
a. means for actuating an operation of the power hand tool,
b. manually operated control means for activating a low current electric command signal maintained below the necessary current flow for operating a solenoid means,
c. said command signal electrically flowing through said manually operated control means,
d. circuit means separate from the manually operated control means and including amplifying means for providing a higher current operational signal to said tool operation actuating means,
e. said amplifying means being responsive to the low current electric command signal when said command signal is activated by said control means to cause said higher current operational signal to operate said tool actuating means.

60. A control assembly as defined in claim 59 wherein
said power tool includes a rotatable tool member mounted in said hand-piece unit and an air driven motor for rotating said tool member,
said finger-tip control means includes a variable electric resistive element providing a variable current input signal for controlling the rotational speed of the tool member and,
said amplifying means being effective to amplify said low current electric input signal and said circuit means including switching means for receiving an amplified current drive signal from said amplifying means and transmitting said higher current operational signal to said air driven motor.

61. A control assembly as defined in claim 59 wherein
said power tool includes a rotatable tool member and an air driven motor for rotating said tool member,
said control means includes a potentiometer having a variable resistance for providing a variable low current electric input signal and
said amplifying means includes an amplifyer means which is responsive to said variable low current input signal and maintains a higher current operational signal that is proportional to said input signal provided by the linear potentiometer.

62. A control assembly as defined in claim 61 wherein
said amplifier means comprises a servo amplifyer which uses feed-back to maintain the current operational signal proportional to the current input signal.

63. A control assembly as defined in claim 59 wherein
said power tool is a dental device having an air driven motor for tool members rotatably mounted in said hand-piece unit,
means for providing cooling water to the rotating tool members and
means for providing syringe water.

64. A control assembly as defined in claim 63 wherein
said actuating means includes means for operating said air driven motor, means for operating said cooling water means and means for operating said syringe water means,
said circuit means includes switching means for receiving an amplified current drive signal from said amplifying means and transmitting said higher current operational signal to each said operating means.

65. A control assembly as defined in claim 63 wherein
said actuating means includes means for operating said air driven motor, means for operating said cooling water means and means for operating said syringe water means,
said amplifying means comprises first amplifying and switching means for providing said higher current operational signal to the operating means for said air driven motor, second amplifying and switching means for providing asid higher current operational signal to the operating means for the cooling water, and third amplifying and switching means for providing said higher current operational signal to the operating means for the syringe water.

66. An assembly as defined in claim 65 wherein
said finger-tip control means includes a potentiometer having a variable low current electric input signal,
said first amplifying and switching means includes means for sensing said variable low current input signal and maintaining a higher current operational signal that is proportional to said variable low current input signal provided by the potentiometer.

67. A control assembly as defined in claim 65, wherein
each said switching means prevents current flow when said finger-tip control means is released thereby deactivating said actuating means.

68. A control assembly as defined in claim 65, wherein
each said amplifying means includes an operational amplifier having a current gain sufficient to provide a current drive signal to each said switching means.

69. A control assembly as defined in claim 65, wherein
said finger-tip control means includes a variable electric resistive element providing a variable low current electric input signal for controlling the rotational speed of the tool member and
said first amplifying means includes means for sensing said variable low current input signal and maintaining a higher current operational signal that is proportional to said variable low current input signal provided by the variable electric resistive element.

70. A control assembly as defined in claim 63, wherein
said tool actuating means includes a solenoid means for operating each said operation of the dental device and air control valve means for controlling an air supply to the air driven motor and first water control valve means for controlling the flow of cooling water and second water control valve means for controlling the flow of syringe water.

71. A control assembly as defined in claim 70, wherein
said air control valve means is a variable air control valve and
said solenoid means includes a rotary solenoid for adjusting said variable air control valve,
said finger-tip control means includes a potentiometer having a variable resistance and
said amplifying means includes an amplifier means which is responsive to said low current electric input signal and maintains a higher current operational signal that is proportional to said current input signal provided by the potentiometer.

72. A control assembly as defined in claim 63, wherein
said dental device includes a light source means mounted on the hand-piece unit and
said finger-tip control means includes a manually operated switch which turns the low current electric signal on and off thereby turning the higher current operational signal on and off with respect to the light source means.

73. A control assembly as defined in claim 72, wherein
said light source means includes a fiber-optic bundle mounted in the hand-piece unit and lens means for dispersing light transmitted by the fiber-optic bundle.

74. A control assembly as defined in claim 59, wherein
said hand-piece unit includes means for mounting a dental hand mirror.

75. A control assembly as defined in claim 59, wherein
said hand-piece unit is completely separated from the power tool.

76. A control assembly as defined in claim 59, wherein
said power tool includes a rotatable tool member mounted in a first hand-piece unit having a first finger-tip control mechanism and a second hand-piece unit having a second finger-tip control mechanism.

77. A control assembly as defined in claim 76, wherein
said circuit means includes a switch for engaging one of said first and second hand-piece units with an electric current source.

78. A control assembly as defined in claim 59, wherein
said power tool includes a tool member mounted in said hand-piece unit and
a light source means is mounted on the hand-piece unit for dispersing light toward the tool member.

79. A control assembly as defined in claim 78, wherein
the power tool is a dental device having a rotatable tool member.

80. A control assembly as defined in claim 79, wherein
said light source means includes a fiber-optic bundle mounted in the hand-piece unit and lens means for dispersing light transmitted by the fiber-optic bundle.

81. A control assembly as defined in claim 59 wherein
said control means includes an isolation transformer, rectifying means and regulating means for providing said low current electric signal.

82. A control system as defined in claim 59 wherein said low current command signal is maintained at up to about 10 micro amps.

* * * * *